(12) United States Patent
Vidalakis et al.

(10) Patent No.: US 9,574,244 B2
(45) Date of Patent: Feb. 21, 2017

(54) MOLECULAR METHOD FOR UNIVERSAL DETECTION OF CITRUS VIROIDS

(71) Applicant: The Regents of the University of California, Oakland, CA (US)

(72) Inventors: Georgios Vidalakis, Riverside, CA (US); Jinbo Wang, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 53 days.

(21) Appl. No.: 14/341,581

(22) Filed: Jul. 25, 2014

(65) Prior Publication Data

US 2015/0050639 A1 Feb. 19, 2015

Related U.S. Application Data

(62) Division of application No. 13/670,812, filed on Nov. 7, 2012, now Pat. No. 8,815,547.

(60) Provisional application No. 61/556,634, filed on Nov. 7, 2011.

(51) Int. Cl.
| | | |
|---|---|---|
| *C12P 19/34* | (2006.01) | |
| *C12Q 1/70* | (2006.01) | |
| *C12Q 1/68* | (2006.01) | |

(52) U.S. Cl.
CPC ............. *C12Q 1/701* (2013.01); *C12Q 1/6895* (2013.01); *C12Q 2600/112* (2013.01); *C12Q 2600/158* (2013.01); *C12Q 2600/16* (2013.01)

(58) Field of Classification Search
CPC . C12Q 1/6895; C12Q 1/701; C12Q 2600/112; C12Q 2600/158; C12Q 2600/16
See application file for complete search history.

(56) References Cited

FOREIGN PATENT DOCUMENTS

JP 2000184893 * 7/2000

OTHER PUBLICATIONS

Tessitori et al., Sixteenth IOCV conference, Short communications, 456-459, 2005.
Rizzo et al., Plant Pathology, vol. 58, pp. 181-185, 2009.
George Vidalakis, California Citrus Nursery Board, https://s3.amazonaws.com/bizba6/share/clients/CCNB/reports/Vidalakis+-+Future+2010., pp. 1-3, Feb. 6, 2011.

* cited by examiner

*Primary Examiner* — Cynthia B Wilder
(74) *Attorney, Agent, or Firm* — Kilpatrick Townsend & Stockton LLP

(57) ABSTRACT

The present invention provides methods for universally detecting citrus viroids in plant material such as germplasm. In particular embodiments, the invention enables the determination of citrus viroid infection and plant resistance. Accordingly, the present method provides methods for improved universal detection of any citrus viroid.

16 Claims, 8 Drawing Sheets

```
ACAAGG-CAGGGAGGAGACTTACCTGAGAAAGGAGCCCCGGGGCAACTCTTCTCAGAATC 101
ACAAGG-CAGGGAGGT-ACTTACCTGAGAAAGGAGCCCCGGGGCAACTCTTCTCAGAATC 100
ACAAGG-CAGGAAGGAGACTTACCTGAGAAAGGAGCCCCGGGGCAACTCTTCTCAGAATC 102
ACAAGGGCAGGAG--AGACTTACCTGAGAAAGGAGCCCCGGGGCAACTCTTCTCAGAATC 100
AGAGGC-GGCGGGGGAAGAAGTCCT--TCAGGGATCCCCGGGGAAAC-CTGGAGGAAGTC 116
AGAGGC-GGCGGGG-AAGAAGTCCT--TCAGGGATCCCCGGGGAAAC-CTGGAGGAAGTC 115
AGAGGC-GGCGGGGGAAGAAGTCCT--TCAGGGATCCCCGGGGAAAC-CTGGAGGAAGTC 116
ACAGCT-TGTGGAGGGAACATACCTGAAGAGGGATCCCCGGGGAAAT-CTCTTCAGACTC 89
 * *,    . *..    ..: :***   *,*** ******,**  **  :  ,.* **

CAG--CGAGAGGCGTAGG----AGAGAGGGCCGCGGTGCTCTGGAGTAGAG----GCTTC 151
CAG--CGAGAGGCGTAGG----AGAGAGGGCCGCGGTGCTCTGGAGTAGAG----GCTTC 150
CAG--CGGG-GGCGTGG----AGAGAGGGCCGCGGTGCTCTGGAGTAGAG----GCTTC 150
CAG--CGGG-GGCGTGG----AGAGAGGGCCGCGGTGCTCTGGAGTAGAG----GCTTC 148
GAGGTCGGGGGGG-ACAGCTGCTTCGGTCGCCGCGGATCACTGGCGTCCAGCGGAGAAAC 175
GAGGTCGGGGGGGTACAGCTGCTTCGGTCGCCGCGGATCACTGGCGTCCAGCGGAGAAAC 175
GAGGTCGGGGGGG-ACAGCTGCTTCGGTCGCCGCGGATCACTGGCGTCCAGCGGAGAAAC 175
GTCGAGGGGAGGG------------CGCCGCGGATCACTGGCGTCCAGCACCGGAAC 134
 :    *,* **              *******: *:****,**, **    *  ::*
```

MOLECULAR METHOD FOR UNIVERSAL DETECTION OF CITRUS VIROIDS

CROSS-REFERENCE TO RELATED APPLICATIONS

This application is a Divisional of U.S. application Ser. No. 13/670,812 filed on Nov. 7, 2012, which claims priority to U.S. Provisional Application No. 61/556,634, filed on Nov. 7, 2011, the disclosure of which is hereby incorporated by reference for all purposes.

REFERENCE TO A SEQUENCE LISTING

This application includes a Sequence Listing as a text file named "SEQTXT_81906-210610US-855858" created Nov. 6, 2012 and containing 3,517 bytes. The material contained in this text file is incorporated by reference in its entirety for all purposes.

BACKGROUND OF THE INVENTION

Citrus is susceptible to numerous disease caused by plant pathogens. Seven distinct viroid species representing four genera of the Pospiviroidae family have been identified: Citrus exocortis viroid (CEVd, genus *Pospiviroid*), Hop stunt viroid (HSVd, genus *Hostuviroid*), Citrus bark cracking viroid (CBCVd, genus *Cocadviroid*), and Citrus bent leaf viroid (CBLVd, genus *As*), Citrus dwarfing viroid (CDVd), Citrus viroid V (CVd-V) and Citrus viroid VI (CVd-VI).

Viroids are nonencapsidated, small circular, single-stranded RNAs that replicate autonomously when inoculated in their host plants. Most citrus viroids are widespread, usually occurring as complex mixtures that co-infect the same plant. Citrus viroids can elicit diseases in sensitive hosts such as exocortis and cachexia or affect tree size and crop (see, e.g., Semancik et al., *J. Gen. Virol.*, 69:3059-3068 (1988); Semancik and Weathers, *Virology*, 46:456-466 (1972); and Verniere et al., *Plant Dis.*, 88:1189-1197 (2004)).

Economic loss due to these diseases can be severe and is of particular concern in states such as California and Florida, which produce most of the United States' supply of citrus fruits. To prevent the spread of citrus disease, federal and state agencies have adopted registration programs that routinely performs time-consuming and costly pathogen tests to evaluate host resistance and viroid accumulation in plants and germplasm. Pathogen-infected germplasms must undergo treatment or removal from the certified registration programs regardless of the pathogen species, strain or isolate. Since agencies regularly screen thousands of samples, there remains an unmet need for an efficient and reliable method for the universal detection of all citrus viroid.

Currently, the most popular or standard molecular citrus viroid detection method is the conventional reverse transcription polymerase chain reaction (RT-PCR). Several RT-PCR protocols are available today for the detection of citrus viroids (Bernard, L. and Duran-Vila, N., Mol. Cell. Probes, 20:105-113 (2006); Ito et al., J. Virol. Methods, 106: 23.5-239 (2002)). However, in principal, the conventional RT-PCR requires seven different protocols with seven different sets of viroid specific primers for the detection of all known citrus viroids. In addition, methods such as gel electrophoresis are needed to visualize the results.

Nucleic acid-detection methods (e.g., microarray, real-time quantitative PCR (RT-qPCR)) have been used for real time detection of viral and bacterial pathogens (see, e.g., Aldea et al., *J. Clin. Microbiol.*, 40:1060-2; Nadkarni et al., *Microbiology*, 148:257-66 (2002); Young et al., *J. Virol. Methods*, 103:27-39 (2002); Trottier et al., *J. Virol. Methods*, 103:89-99 (2002)). Real-time PCR technology allows for accurate quantitation of gene expression and gene expression patterns in multiple samples over a large dynamic range. The technology is used to analyze and indirectly quantitate mRNA expression levels by measuring the amount of amplified cDNA, rather than the amount of RNA in a sample. Real-time quantitative PCR is dependent on reverse transcription and PCR amplification, whereby a fluorescent signal incorporated into double-stranded DNA (dsDNA) is detected in each amplification cycle.

The present invention provides a method for the universal detection of all known citrus viroids using a multiplex of RT-qPCR assays. The present invention provides a universal, accurate, efficient, cost-effective, and quick method of detecting any citrus viroid pathogen. The method can be easily adapted for high throughput screenings.

BRIEF SUMMARY OF THE INVENTION

In one aspect, the present invention provides methods for detecting a citrus viroid in a plant sample comprising: (a) extracting RNA from said sample; (b) detecting the presence or absence of amplification products from a real-time quantitative PCR assay comprising said RNA of step (a) as a template and degenerate oligonucleotide primer pairs of SEQ ID NOS: 1 and 2, and (c) detecting the presence or absence of amplification products from a real-time quantitative PCR assay comprising said RNA of step (a) as a template and degenerate oligonucleotide primer pairs of SEQ ID NOS: 3 and 4; and (d) determining the presence or absence of a citrus viroid infection in said sample originating from any citrus viroid species based on the presence or absence of amplification products. In other aspects, the method further comprises destroying the plant sample and the plant from which said sample was isolated if the presence of a citrus viroid infection in said sample is determined.

In some instances, said citrus viroid is selected from a group comprising Citrus exocertis viroid, Hop stunt viroid, Citrus bark cracking viroid, Citrus bent leaf viroid, Citrus dwarfing viroid, Citrus viroid V, and Citrus viroid VI. In some instances, said amplification products comprise a detectable label. In some instances, said a detectable label comprises a fluorophore. In some instances, said sample is plant material. In some aspects, said plant material is selected from a group consisting of seed, foliage, limbs, trunk, bark, rootstock, fruit, germplasm, propagule, cuttings, and budwood.

In some aspects of the invention prior to steps (b) and (c), said RNA and said degenerate oligonucleotide primer pair of SEQ ID NOS: 1 and 2 are held in a high temperature RNA denaturation step. In some aspects of the invention prior to step (b) and (c), said RNA and said degenerate oligonucleotide primer pairs of SEQ ID NOS: 3 and 4 are held in a high temperature RNA denaturation step. In some instances, said high temperature RNA denaturation step comprises holding an admixture comprising said RNA and said primers at a temperature of at least 80° C. for at least 5 minutes, and then at less than 5° C. for at least 2 minutes.

In one aspect, the invention provides diagnostic reaction mixture compositions for amplifying and detecting RNA of citrus viroids of *Apscaviroid* genus comprising a nucleic acid sample and at least one degenerate primer pair which amplifies a Citrus bent leaf viroid sequence (SEQ ID NO: 5).

In some instances, said degenerate primer pair comprises SEQ ID NO: 1 and SEQ ID NO: 2. In another aspect, the invention provides a diagnostic reaction mixture composition for amplifying and detecting RNA of citrus viroids of *Hostuviroid, Pospiviroid* or *Cocadviroid* genus comprising a nucleic acid sample and at least one degenerate primer pair which amplifies a Hop stunt viroid sequence (SEQ ID NO: 6) In some instances, said degenerate primer pair comprises SEQ ID NO: 3 and SEQ ID NO: 4.

In some aspects, the diagnostic reaction mixture of the invention comprises a nucleic acid sample, a degenerate primer pair of SEQ ID NOS: 1 and 2, and/or a degenerate primer pair of SEQ ID NOS: 3 and 4.

In some instances, said nucleic acid sample of the diagnostic reaction mixture is extracted from plant material, wherein said plant material is selected from a group consisting of seed, foliage, limbs, trunk, bark, rootstock, fruit, germplasm, propagule, cuttings, and budwood. In other instances, the mixture composition further comprising dNTPs, a buffer, thermostable DNA polymerase, reverse transcriptase, a fluorophore, or a stabilizer.

In one aspect, the invention provides a kit comprising a degenerate primer pair of SEQ ID NOS: 1 and 2 and/or SEQ ID NOS: 3 and 4. In some instances, the kit further comprises dNTPs, a buffer, thermostable DNA polymerase, reverse transcriptase, a fluorophore, or a stabilizer.

BRIEF DESCRIPTION OF THE DRAWINGS

FIG. 1 shows the conversed sequences of the citrus viroids in the Apsca group: Citrus dwarfing viroid, Citrus viroid VI, Citrus viroid V and Citrus bent leaf viroid. The sequences are listed from top to bottom in the following order: GenBank Accession Nos: 576452, GQ206212, AB019508, EF617306, M74065, and AB019509. The black bars note the corresponding viroid genome regions that correspond to the forward and reverse primers. An asterisk notes a conserved nucleic acid.

FIG. 2 shows the conserved sequences of the citrus viroids in the non-Apsca group: Hop stunt viroid, citrus exocortis viroid and citrus back cracking viroid. The sequences are listed from top to bottom in the following order: GenBank Accession Nos: AF131248, AF131252, AF131249, GQ260209, J02053, GU295988, and M30868. The black bars note the corresponding viroid genome regions that correspond to the forward and reverse primers. An asterisk notes a conserved nucleic acid.

DETAILED DESCRIPTION OF THE INVENTION

I. Introduction

Figure 3:
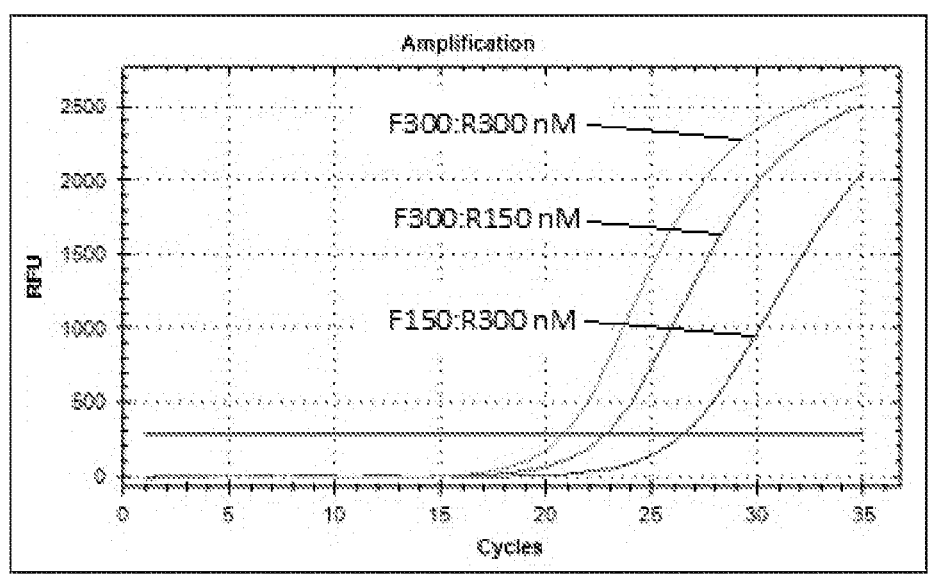
FIG. 3 shows the performance of the Apsca group primer pair on SYBR Green RT-qPCR with different forward and reverse primer concentrations.

Viroid species of the genera *Pospiviroid* (Citrus exocortis viroid, CEVd), *Hostuviroid* (Hop stunt viroid, HSvd), *Cocadviroid* (Citrus bark cracking viroid, CBCVd), and *Aspscaviroid* (Citrus bent leaf viroid, CBLVd, Citrus dwarfing viroid, CDVd, Citrus viroid V, CVd-V, and Citrus viroid VI, CVd-VI) can cause widespread infections of citrus plants, resulting in disease and reduced tree size and crop.

The present invention provides methods and kits for detecting citrus viroids in plant samples. The invention is based in part, upon the discovery that all citrus viroids can be detected and quantified using two sets of degenerate primer pairs in methods based on real-time quantitative PCR.

The present inventors have discovered that viroids of the *Apscaviroid* genus share a consensus sequence that can be amplified using a set of degenerate oligonucleotide primer pairs and quantified in a RT-qPCR assay. In addition, the present inventors also have discovered that viroids of the *Pospiviroid, Hostuviroid* and *Cocadviroid* genera all share a conserved sequence that can be amplified and quantified using another set of degenerate oligonucleotide primer pairs in a separate RT-qPCR assay. The present invention provides a method for the universal detection of all citrus viroids in biological samples.

The ability to detect all citrus viroids by virtue of performing the method of the invention is useful for diagnosing citrus viral infections in plant material and determining the extent of an infection.

II. Definitions

As used herein, the following terms have the meanings ascribed to them unless specified otherwise.

The term "citrus viroid" describes a type of citrus pathogen that has been classified in belonging to any of the following genera: *Pospiviroid, Hostuviroid, Cocadviroid, Aspscaviroid*, and the like. Non-limiting examples of a citrus viroid include citrus exocortis viroid, hop stunt viroid and variants (CV-IIa, CV-IIb, CV-IIc, Ca-903 and CA-909), citrus bark cracking viroid, citrus bent leaf viroid, citrus dwarfing viroid, citrus viroid I, (CVd-I-LSS, CV-Ia, CV-Ib), citrus viroid III (CV-IIIa, CV-IIIB, and CV-IIIc), citrus viroid V, and citrus viroid VI.

The terms "real-time quantitative polymerase chain reaction," "RT-qPCR," "quantitative real-time polymerase chain reaction," "real-time polymerase chain reaction," "real time PCR," and "kinetic polymerase chain reaction" refer to a laboratory technique based on polymerase chain reaction, which is used to simultaneously amplify, detect and quantify a targeted nucleic acid molecule, such as DNA and cDNA, in a sample. The technique can be used to correlate the amount of target RNA transcript present in the sample. Non-limiting examples of methods for detecting of the amplification products in RT-qPCR include non-specific fluorescent dyes that intercalate with any double-stranded DNA, and sequence-specific probes comprising oligonucleotides that are labeled with a fluorescent reporter which permits detection only after hybridization of the probe with its complementary DNA target.

The term "one step RT-qPCR" refers to a technique that combines reverse transcription, and PCR amplification in a single reaction vessel. It is a method used to quantify a specific messenger RNA and non-coding RNA transcript present in a sample.

The term "two step RT-qPCR" includes an assay that begins with first-strand synthesis comprising the reverse transcription of RNA into cDNA using a reverse transcriptase, and then polymerase chain reaction (PCR) of the synthesized cDNA to amplify a specific gene sequence.

The term "reverse transcriptase" describes a class of polymerases characterized as RNA-dependent DNA polymerases. All known reverse transcriptases require an oligonucleotide primer (e.g., random primer, oligo dT, and sequence-specific primer) to synthesize a DNA transcript from an RNA template.

The term "DNA polymerase" refers to an enzyme that can assemble new DNA strands from nucleotides by using a single stranded DNA template and DNA oligonucleotides. Non-limiting examples of thermostable DNA polymerases include Taq polymerase and variants thereof.

The term "RNA" refers to all RNA molecules including, but not limited to messenger RNA, total RNA, and double-stranded RNA.

The term "fluorophore" refers to a chemical group or molecule responsible for fluorescence (e.g., the ability to absorb energy of a specific wavelength and re-emit energy at a different wavelength. Non-limiting examples of a fluorophore include fluorescent dyes (e.g., fluoroscein, rhodamine, cyanine, hydroxycoumarin, R-phycoerythrin, BODIPY, Alexa Fluor, Cy3, and Cy5), fluorescent proteins (e.g., mCFP, mStrawberry, EGFP, Topaz, Venus, Emerald, and EYFP), fluorescent aptamers, fluorescent nucleic acid probes (e.g., SYBR green, TOTO-1, SYTOX blue, and SYTOX Orange, and Acridine Orange), and quantum dots.

III. Detailed Description of Embodiments

The present invention provides methods and kits for universally detecting any citrus viroid in a plant sample comprising: (a) extracting total RNA from said sample; (b) performing two real-time quantitative PCR assays using two sets degenerate oligonucleotide primer pairs; and (d) determining the presence of a citrus viroid infection in said sample originating from any citrus viroid species by comparing to control samples.

In one aspect, the present invention provides a method for detecting all citrus viroids including but not limited to, Citrus exocortis viroid (CEVd, genus *Pospiviroid*), Hop stunt viroid (HSVd, genus *Hostuviroid*), Citrus bark cracking viroid (CBCVd, genus *Cocadviroid*), and Citrus bent leaf viroid (CBLVd, genus *Apscaviroid*), Citrus dwarfing viroid (CDVd, genus *Apscaviroid*), Citrus viroid V (CVd-V, genus *Apscaviroid*) and Citrus viroid VI (CVd-VI, genus *Apscaviroid*).

In this aspect, the method comprises: (1) a real-time quantatitve PCR assay using degenerate oligonucleotide primer pairs for the genus *Apscaviroid* (SEQ ID NOS: 1 and 2); and/or (2) a real-time quantatitve PCR assay using degenerate oligonucleotide primer pairs specific for the genera *Pospiviroid, Hostuviroid*, and *Cocadviroid* (SEQ ID NOS: 3 and 4).

In another aspect, the present invention provides a kit for detecting all citrus viroids including but not limited to, Citrus exocortis viroid (CEVd, genus *Pospiviroid*), Hop stunt viroid (HSVd, genus *Hostuviroid*), Citrus bark cracking viroid (CBCVd, genus *Cocadviroid*), and Citrus bent leaf viroid (CBLVd, genus *Apscaviroid*), Citrus dwarfing viroid (CDVd, genus *Apscaviroid*), Citrus viroid V (CVd-V, genus *Apscaviroid*) and Citrus viroid VI (CVd-VI, genus *Apscaviroid*).

In this aspect, the kit comprises: (1) a degenerate oligonucleotide primer pairs for detecting citrus viroids of the genus *Apscaviroid* in a real-time quantitative PCR assay; and/or (2) a degenerate oligonucleotide primer pairs for detecting citrus viroids of the genera *Pospiviroid, Hostuviroid*, and *Cocadviroid* in a real-time quantitative PCR assay.

The present invention provides methods to diagnose infection with citrus viroid pathogens. By identifying infected plants, the methods described herein provide invaluable information to assess host resistance and viroid accumulation. In some embodiments, the methods can be used in high-throughput screenings of thousands of plant samples in regulatory and research programs.

In one aspect of the invention, the presence of any citrus viroid in biological samples suspected of being infected by a citrus viroid can be determined. Regardless of the type of viroid, all citrus viroids can be detected using methods of the present invention. In another aspect, the methods of the invention comprise detecting citrus viroids of the *Apscaviroid, Hostuviroid, Pospiviroid* and *Cocadviroid* genera. In yet another aspect, the methods comprise detecting citrus viroids of the *Apscaviroid* genus in a RT-qPCR assay and detecting citrus viroids of the *Hostuviroid, Pospiviroid* and *Cocadviroid* genera in another RT-qPCR assay.

In another aspect of the invention, the presence and/or level of any citrus viroid in a plant sample can be determined by detecting and measuring RNA transcripts of all citrus viroids using two sets of degenerate oligonucleotide primer pairs. It is known by those skilled in the art that determining levels of RNA transcripts can be performed using method such as, but not limited to microarray, RNA-seq, immunocapture-PCR (IC-PCR), QuantiGene Plex 2.0 Assay (Affymetrix), and real-time quantitative PCR.

A. Real-Time Quantitative PCR

The methods and compositions of the invention can be used in real-time quantitative PCR methods. As is known to those skilled in the art, real-time quantitative PCR methods combine PCR amplification and detection of the target PCR product (e.g., amplicon) in a single step. Non-limiting examples of real-time quantitative PCR methods include sequence-dependent detection assays (e.g., Taqman gene expression assays) and sequence-independent detection assays (e.g., SYBR Green qRT-PCR assays). When PCR products are fluorescent and fluorescence is plotted against cycle number, the accumulation of PCR products can be depicted as an amplification curve. This amplification curve has three segments: an early background phase, an exponential growth phase (e.g., log phase) and a plateau (e.g., endpoint) phase. In a RT-qPCR assay, data regarding the concentration of the PCR product is collected from each PCR amplification cycle. Data from the exponential cycles of PCR can be used to determine the amount of PCR product present during the exponential phase, and by extrapolation, the initial amount of the template in each PCR reaction.

Sequence-independent detection assays rely on a fluorescent dye that bind to all dsDNA molecules regardless of sequence. Non-limiting examples of a fluorescent dye for these assays include SYBR Green, SYBR Gold, Oxazole Yellow, Thiazole Orange, PicoGreen, BOXTO, SYTO-13, SYTO-82, and any fluorescent dye that can bind dsDNA. For instance, SYBR Green I emits fluorescence when it binds to dsDNA and is excited by blue light. Thus, the amount of target product amplified during PCR can be correlated with an increase in SYBR Green I signaling as measured at a wavelength of 530 nm at the end of the extension phase of each PCR cycle. To characterize the target PCR product and determine if it is free of non-specific byproducts (e.g., non-specific PCR products, primer dimers, and other double-stranded artifacts), a melting curve analysis is performed subsequent to the PCR run. During a melting curve analysis, the qPCR reaction mixture is slowly heated to 95° C., which causes dsDNA to melt. A sharp decrease in SYBR Green I fluorescence occurs when the temperature reaches the melting temperature (Tm; temperature when 50% of the DNA is double-stranded and 50% is melted) of the target PCR product present in the reaction. A plot of a derivative melting curve can be used to determine if only one amplicon is present in the reaction, as represented by one melting peak. The presence of additional melting peaks represent primer-dimers or other non-specific products in the reaction.

Sequence-dependent detection assays are different from a sequence-independent detection assay in that they rely on oligonucleotide probes (e.g., hydrolysis probes, hybridization probes (Taqman probes or Molecular Beacons), or single-labeled probes) that hybridize to their complementary sequence in the target PCR product and detect only this specific product. The probes are coupled to fluorophores and specific hybridization between probe and target PCR product is required to generate a fluorescent signal. This method significantly reduces background fluorescence and false positives. In a Taqman probe-based assay, a fluorescent reporter dye (e.g., 6-carboxyfluorescein (FAM), tetrachlorofluorescin (TET)) and a quencher dye (e.g., tetramethylrhodamine (TAMRA), dihydrocyclopyrroloindole tripeptide minor groove binder (MGB)) are attached to the 5' and 3' ends of a Taqman probe, respectively. When the probe is intact, the reporter dye emission is quenched by the quencher. During each PCR cycle, DNA polymerase of the reaction cleaves the reporter dye from the probe. And once separated from the quencher, the reporter dye emits its characteristic fluorescence which can be detected by real-time PCR instruments. Non-limiting examples of real-time PCR instruments include LightCycler 480 system (Roche, Indianapolis, Ind.), CFX Touch™ Real-Time PCR Detection system (Bio-Rad, Hercules, Calif.), StepOne Real-Time PCR System (Applied Biosystems, Foster City, Calif.) and Mastercycler ep realplex (Eppendorf, Hamburg, Germany).

B. Universal Detection of Citrus Viroids

In one embodiment, methods of the present invention comprise detecting and determining the level of viroids of the *Apscaviroid* genus (referred herein as Apsca Group) using one set of degenerate oligonucleotide primer pairs, and viroids of the *Hostuviroid, Pospiviroid* and *Cocadviroid* genera (referred herein as non-Apsca group) using another set of degenerate oligonucleotide primer pairs. In another aspect, the methods further comprise performing an RT-qPCR assay using the set of degenerate primer pairs for the *Hostuviroid, Pospiviroid* and *Cocadviroid* genera; and another RT-qPCR assay using the set of degenerate primer pairs for viroids of the *Apscaviroid* genus.

In some embodiments, the set of degenerate primer pairs used for detecting viroids of the Apsca group comprise SEQ ID NOS: 1 and 2, and the set of degenerate primer pairs used for detecting viroids of the non-Apsca Group comprise SEQ ID NOS: 3 and 4. Table 1 includes exemplary examples of the degenerate primers used in the methods of the present invention.

TABLE 1

| Name in Example 1 | SEQ ID NO: | Primer | Oligonucleotide primer sequence (5'→3') R = A or G Y = C or T M = A or C K = G or T S = C or G W = A or T B = C or G or T H = A or C or T D = A or G or T V = A or C or G |
|---|---|---|---|
| Apsca Group F-3-25 | SEQ ID NO: 1 | Forward | GARMMWYCKTGTGGTTCCTGTGG |
| Apsca Group R-232-212 | SEQ ID NO: 2 | Reverse | HYVDWHGTCCGCTCGACTAGC |
| Non-Apsca Group F-71-87 | SEQ ID NO: 3 | Forward | ARGGAKCCCCGGGGMAA |
| Non-Apsca Group R-146-125 | SEQ ID NO: 4 | Reverse | CTSKACKCCAGWGMWCCGCGGC |

| GenBank Accension No. | SEQ ID NO: | Citris Viroid Name | Sequence |
|---|---|---|---|
| M74065 | SEQ ID NO: 5 | CBLVd | 1 cggagacttc ttgtggttcc<br>tgtggtgaca cccctcaagc<br>41 cctacctgcg aaagaaaaaa<br>gtgttagaag gcggcagagg<br>81 agctgactgg tcgtcgtcga<br>cgaaggctcg tcagctgcgg<br>121 aggttggggt cgactggctc<br>cggtggcgaa gttgagctct<br>161 gctcttctaa gctgtaacgg<br>accggtcccc ttcacccgag<br>201 cgctgcttgc cgctagtcga<br>gcggacttcc aagtctccct<br>241 cccgagccgc ttttcttttc<br>tacctaattt ccgtagcagc<br>281 ggggagaggg tgaagcccct<br>gaaccctga gggctcct |
| AF131248 | SEQ ID NO: 6 | HSVd | 1 ctggggaatt ctcgagttgc<br>cgcatgggca agcaaagaaa<br>41 aaacaaggca gggaggagac<br>ttacctgaga aaggagcccc<br>81 ggggcaactc ttctcagaat<br>ccagcgagag gcgtaggaga<br>121 gagggccgcg gtgctctgga<br>gtagaggctt ctagcttcga<br>161 aacaccatcg atcgtccctt<br>cttcttttac cttctcctgg<br>201 ctcttcgagt gagacgcgac<br>cggtggcatc acctctcggt<br>241 tcgtcttcca acctgctttt<br>tgtctatctg agcctctgcc<br>281 cggatcctc tcttgagccc<br>ct |

In one aspect of the present invention, the degenerate primers of SEQ ID NOS: 1 and 2 hybridize (are complementary or anneal) to a conserved sequence located in the CBLVd, CDVd, CVd-V and CVd-VI genomes. The Apsca group primers (SEQ ID NOS: 1 and 2; see Table 1) are used to detect CBLVd, CDVd, CVd-V and CVd-VI viroid species of the *Apscaviroid* genus. In some embodiments, the degenerate primers correspond to a region of the CBLVd sequence (SEQ ID NO: 5; GenBank Accession No. M74065) spanning from position 3 to position 25 (forward primer) and from position 232 to positions 212 (reverse primer). In other aspect, the degenerate primers of SEQ ID NOS: 3 and 4 hybridize to a conserved sequence located in the CEVd, HSVd and CBCVd genomes. The Non-Apsca group primers (SEQ ID NOS: 3 and 4; see Table 1) are used to detect CEVd, HSVd and CBCVd viroids, including all citrus variants of HSVd (e.g., IIa, IIb and IIc), of the *Pospiviroid*, *Hostuviroid*, and *Cocadviroid* genus, respectively. In some embodiments, the degenerate primers correspond to a region of the HSVd sequence (SEQ ID NO: 6; GenBank Accession No. AF131248) spanning from position 71 to position 87 (forward primer) and position 146 to position 125 (reverse primer). As is known by those skilled in the art, sequence-specific degenerate oligonucleotide primers are available from, e.g., Invitrogen (Carlsbad, Calif.), Integrated DNA Technologies (Coraville, Iowa) and Sigma-Aldrich (St. Louis, Mo.).

In another embodiment, the method comprises extracting RNA from plant material (e.g., seed, foliage, limbs, trunk, bark, rootstock, fruit, germplasm, propagule, cuttings, and budwood). The plant material can be frozen or fresh. The plant material can be citrus propagative material. Methods for extracting RNA from a plant sample are known to those skilled in the art and are described in Bilgin et al., *Nature Protocols*, 4:333-340, (2009); Berendzen et al., *Plant Methods*, 1:4 (2005); Elspeth MacRae, *Methods in Molecular Biology*, vol. 353: *Protocols for Nucleic Acid Analysis by Nonradioactive Probes, Second Edition*, Humana Press, New Jersey, 15-24, (2007); P. Narayanasamy, *Microbial Plant Pathogens-Detection and Disease Diagnosis: Vial and Viroid Pathogens* Vol. 3, Springer, Dordrecht, (2010). Non-limiting examples of commercially available plant RNA extraction kits include RNAeasy Plant Mini Kit (Qiagen, Hilden, Germany), PrepEase Plant Spin Kit (Affymetrix, Santa Clara, Calif.), Agilent Plant RNA Isolation Mini Kit (Agilent Technologies, Santa Clara, Calif.), Plant RNA Isolation Aid (Ambion, Austin, Tex.), and Spectrum Plant total RNA kit (Sigma-Aldrich, St. Louis, Mo.). The extracted RNA can be used as a target RNA template in an RT-qPCR assay.

In some embodiments, the real-time PCR assay comprises a one-step RT-qPCR reaction mixture, wherein said reaction mixture comprises target RNA template, a set of degenerate primers, reverse transcriptase, DNA polymerase, buffer (e.g., balanced combination of $NH_4^+$ and $K^+$ ions), deoxynucleoside triphosphates (dNTPs), and fluorescent dye (fluorophore). The reaction mixture can also include stabilizers of the reaction mixture. In certain instances, the fluorescent dye binds to dsDNA. In other instances, fluorescent dye or fluorescent nucleic acid intercalates into dsDNA. Non-limiting examples of a fluorescent dye or nucleic acid probe include SYBR Green, SYBR Gold, Oxazole Yellow, Thiazole Orange, PicoGreen, BOXTO, SYTO-13, SYTO-82, and variants thereof. One skilled in the art knows that the components of the reaction mixture of a RT-qPCR assay except for the target RNA template and amplification primers are commercially available. Non-limiting examples of commercially available reagents for RT-qPCR assays include iScript One Step RT-PCR kit with SYBR Green (Bio-Rad, Hercules, Calif.), Express SYBR GreenER Universal (Life Technologies, Carlsbad, Calif.), and QuantiFast SYBR Green RT-PCR kit (Qiagen, Hilden, Germany).

In some embodiments, the one-step RT-qPCR reaction mixture comprises 7.4 µl nuclease-free water, 0.6 µl forward primer (equivalent of 300 nM final concentration), 0.6 µl reverse primer (equivalent of 300 nM final concentration), 1.0 µl (equivalent of 25 ng) RNA template, 10.0 µl 2×SYBR Green RT-PCR reaction mix (Bio-Rad, catalog #170-8892), and 0.4 µl iScript reverse transcriptase for one-step RT-PCR (Bio-Rad, catalog #170-8892). The volume of the reaction mixture is adjusted to a total volume of 20.00 In other embodiments, the RT-qPCR reaction mixture comprises an amount of SYBR Green RT-PCR reaction mix equivalent to 10.0 µl 2×SYBR Green RT-PCR reaction mix (Bio-Rad, catalog #170-8892) and an amount of reverse transcriptase equivalent to iScript reverse transcriptase for one-step RT-PCR (Bio-Rad, catalog #170-8892). In some instances, RT-qPCR reaction mixture comprises target RNA template, a set of degenerate oligonucleotide primer pairs (e.g., primers pairs of the Apsca group or primer pairs of the Non-Apsca group) and reagents from a real-time assay kit in amounts as recommended in the manufacturer's instructions.

In some embodiments, the real-time PCR assay further comprises a method of denaturing the target RNA template and the degenerate primer pair of the RT-qPCR reaction mixture in a reaction vessel prior to the addition of thermolabile enzymes (e.g., reverse transcriptase) into the reaction mixture. The method of denaturing comprises the following steps: 1) incubating the reaction vessel at a temperature of at least 80° C. for at least 5 minutes, and 2) incubating the reaction vessel at less than 5° C. for at least 2 minutes. In some embodiments, the first step of the method of denaturing the target RNA comprises incubating the reaction vessel at 80° C., 81° C., 82° C., 83° C., 84° C., 85° C., 86° C., 87° C., 88° C., 89° C., 90° C., 91° C., 92° C., 93° C., 94° C., 95° C. or more for 5, 6, 7, 8, 9, 10, 15, 20, 30 or more minutes. In some embodiments, the second step of the method of denaturing comprises incubating the reaction vessel at 5° C., 4° C., 3° C., 2° C., 1° C., 0° C. or less for 2, 3, 4, 5, 6, 7, 8, 9, 10, 15, 20, 30 or more minutes. Following the method of denaturing the target RNA, the remaining components of the reaction mixture (e.g., SYBR Green RT-PCR reaction mix and reverse transcriptase) are added to the reaction vessel.

In other embodiments, the methods of the present invention comprises performing the following steps in a real-time instrument after denaturing the RNA template as described herein to the reaction mixture comprising the set of Apsca group primers: (a) incubating at 50° C. for 30 minutes, (b) incubating at 95° C. for 5 minutes; (c) incubating at 95° C. for 10 seconds; (d) incubating at 62° C. for 30 seconds; (e) going back to step (c) for an additional 34 cycles; (f) analyzing RT-qPCR assay; (g) incubating at 95° C. for 1 minute; (h) incubating at 55° C. for 1 minute; (i) performing melting curve analysis from 55° C. to 95° with 0.5° C. increments for 10 seconds.

In another embodiment, the method of the present invention comprises performing the following steps in a real-time PCR instrument after denaturing the RNA template as described herein to the reaction mixture comprising the set of Non-Apsca group primers: (a) incubating at 50° C. for 30 minutes; (b) incubating at 95° C. for 5 minutes; (c) incubating at 95° C. for 10 seconds; (d) incubating at 61° C. for 30 seconds; e) going back to step (c) for an additional 34 cycles; (f) analyzing the RT-qPCR assay; (g) incubating at 95° C. for 1 minute; h) incubating at 55° C. for 1 minute; and (i) performing melting curve analysis from 55° C. to 95° with 0.5° C. increments for 10 seconds.

In another aspect of the invention, the methods are utilized in determining the presence of any citrus viroids of the Apsca and Non-Aspca groups as compared to control samples. Detection for plant samples containing CEVd, HSVd, CBCVd, CBLVd, CDVd, CVd-V or CVd-VI, singly or mixed, was specifically confirmed by cloning and sequencing of RT-qPCR products in order to validate the protocol. The inventors have access to a unique 55 year old collection of citrus viroids including several isolates of each viroid species originated from around the world and in some cases unique to California and University of California, Riverside thus were able to validate the method of the invention with in planta samples.

In yet another aspect of the invention, the methods of the present invention are used in determining the levels of any citrus viroids of the Apsca and non-Aspca groups as compared to control samples. In some embodiments, the methods are used in determining the viral load of citrus plant material.

In other embodiments, the RT-qPCR assay comprises two reaction mixtures for a two-step RT-qPCR method, wherein the reverse transcription step and the PCR amplification step are performed separately. Protocols for two-step RT-qPCR are known to those skilled in the art and have been described in detail, e.g., Wacker and Godard, *J. Biomol. Tech.* 16:266-271 (2005); Wong and Medrano, *BioTechniques*, 39:79-85 (2005); and Nolan et al., Nature Protocols, 1:1559-1582, (2006). Non-limiting examples of kits for RT step of a two-step RT-qPCR are High Capacity cDNA Reverse Transcription Kit (Applied Biosystems, Foster City, Calif.), iScript cDNA synthesis kit (Bio-Rad, Hercules, Calif.), and Superscript VILO™ cDNA synthesis kit (Invitrogen, Carlsbad, Calif.). Non-limiting examples of kits for PCR step of a two-step RT-qPCR are Fast SYBR Green Master Mix (Invitrogen, Carlsbad, Calif.), iQ SYBR Green supermix (Bio-Rad, Hercules, Calif.) and SYBR Advantage qPCR Premix (Clontech, Mountain View, Calif.). In some instances, the reverse transcription reaction mixture comprises 1×RT Buffer, 5.5 mM MgCl2, 500 µM per dNTP, 2.5 µM oligonucleotide primers (e.g., random hexamers, oligo dT, sequence-specific reverse oligonucleotide primers, or degenerate reverse oligonucleotide primers), 0.4 U/µl RNase inhibitor, 1.25 U/µl reverse transcriptase, 2.0 µg total RNA, and nuclease-free water to make a final volume of 10 In some instances, the degenerate reverse oligonucleotide primer can be SEQ ID NO: 2 and/or 4. In another aspect of the embodiment, the PCR amplification reaction comprises cDNA generated from a reverse transcription reaction using oligonucleotide primers such as SEQ ID NO: 2 and/or 4, and the set of degenerate oligonucleotide primers for the Apsca group. In another aspect, the PCR amplification reaction comprises cDNA generated from a reverse transcription reaction using oligonucleotide primers such as SEQ ID NO: 2 and/or 4, and the set of degenerate oligonucleotide primers for the Non-Apsca group.

In some instances, the RT-qPCR assay further comprises a fluorescent hybridization probe such as, but not limited to, a Taqman probe, Molecular Beacon, Sunrise primer, Scorpion probes, and Light-up probes. Descriptions of non-limiting examples of fluorescent probes for real-time PCR assays can be found in e.g., Kalternboeck and Wang, *Advances in Clinical Chemistry*, Vol. 40, Elsevier Inc., pp. 219-259, 2005. In some embodiments, the real-time quantitative PCR assay is a Taqman assay or a variant thereof.

IV. Examples

Example 1

RT-qPCR Assays for Universal Detection of Citrus Viroids

The following examples are offered to illustrate, but not to limit, the claimed invention. This example illustrates a method of detecting four species of the *Apscarioid* genus. This example illustrates a method of detecting all other species of citrus viroids, including, but not limited to the *Hostuviroid* genus, *Pospiviroid* genus and *Cocadviroid* genus. This example also illustrates a method of detecting any known citrus viroid in a sample using SYBR Green RT-qPCR assays.

Figure 1:
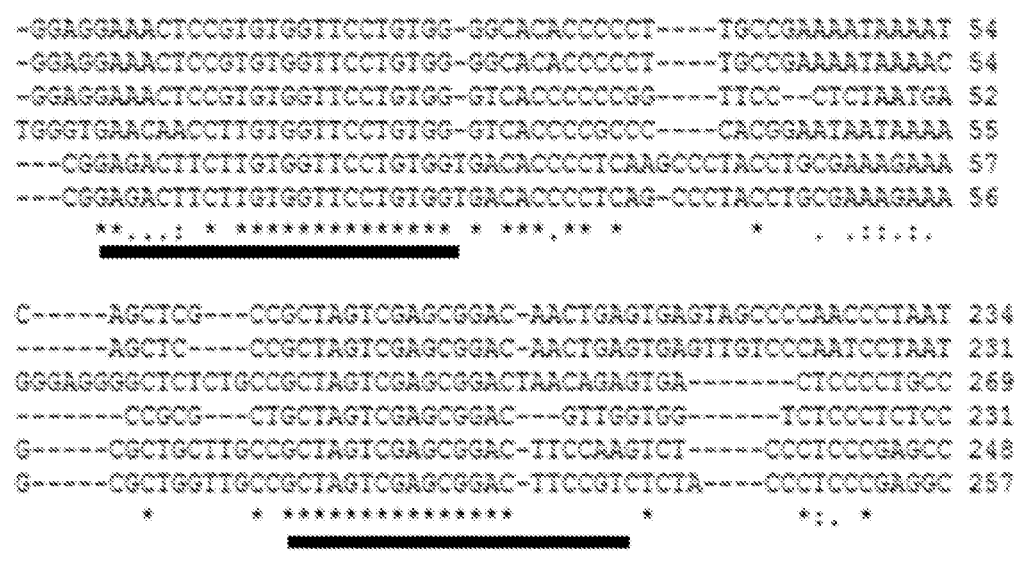

An alignment of the genome of viroids in the *Apscaviroid* genus (e.g., Citrus dwarfing viroid, Citrus viroid VI (CVd-VI), Citrus viroid V (CVd-V), and Citrus bent leaf viroid) revealed a conserved region (FIG. 1). A set of primers referred to as the "Apsca group" was designed based on the conserved sequences (see, FIG. 1 and Table 2). Similarly, an alignment of the genome of viroids in the *Hostuviroid* genus (e.g., Hop stunt viroid), *Pospiviroid* genus (e.g., Citrus exocortis viroid), and *Cocadviroid* genus (e.g., Citrus bark cracking viroid) also revealed a conserved region (FIG. 2). A second set of primers referred to as the "non-Apsca group" was designed based on the conserved sequences (see, FIG. 1 and Table 2). The primer location for the Apsca group corresponds to the CBLVd sequence with GenBank Accession No. M74065.

TABLE 2

Sequences of the forward (F) and reverse (R) degenerate primers in the Apsca group and non-Apsca group.

| RT-qPCR Targets | F and R Primers | Primer sequence (5'→3') | Product size (bp) | Primer Location |
|---|---|---|---|---|
| CBLVd, CDVd, CVd-V, and CVd-VI | Apsca Group F-3-25; SEQ ID NO: 1 | GARMMWYCKTGT GGTTCCTGTGG | 230 | 3-25 |
| | Apsca Group R-232-212; SEQ ID NO: 2 | HYVDWHGTCCGC TCGACTAGC | | 232-212 |
| CEVd, HSVd, and CBCVd | Non-Apsca Group F-71-87; SEQ ID NO: 3 | ARGGAKCCCCGG GGMAA | 76 | 71-87 |
| | Non-Apsca Group R-146-125; SEQ ID NO: 4 | CTSKACKCCAGW GMWCCGCGGC | | 146-125 |

IUPAC nucleotide symbols and notions are used in the Tables 1 and 2.

Two SYBR Green one-step RT-qPCR assays were performed to detect all species of citrus viroids. A SYBR Green one-step RT-qPCR assay was performed to determine if the primers of the Aspca group detected all the citrus viroids of the *Apscarioid* genus. Another SYBR Green one-step RT-qPCR assay was performed to determine if the primers of the non-Apsca group detected all the citrus viroids of the *Hostuviroid*, *Pospiviroid* and *Cocadviroid* genus.

Both SYBR Green one-step RT-qPCR assays utilize a similar diagnostic reaction mixture, except for the primer pairs and the thermal cycling conditions (e.g., thermal cycler program). The steps of the procedure for preparing the diagnostic reaction mixture are listed as follows:

1. Thaw Nuclease-free water, primers solutions, Real Time SYBR Green RT-PCR reaction mix (Bio-Rad iScript One Step RT-PCR kit with SYBR Green), and RNA, and place them on ice.
2. Prepare a mix including Nuclease-free water, forward and reverse primers, according to reaction composition (Table 3).

3. Mix the solution thoroughly, and dispense aliquots of 8.6 μl into PCR tubes.
4. Add 1 μl RNA (25 ng RNA) to the individual PCR tubes.
   Program conventional PCR thermal cycler (Bio-Rad MyCycler thermal cycler) at 80° C. for 5 min and place tubes in. After 5 min program is completed, put tube on ice for 2 min.
   The high-temperature RNA denaturation step is used for viroid RNA which has high G+C content and complex secondary structure. This step is performed before adding the heat sensitive reverse transcriptase enzyme in order to achieve proper cDNA synthesis during RT and subsequent high DNA yields during PCR.
5. Prepare a mix including 2×SYBR Green RT-PCR reaction mix and iScript reverse transcriptase for one-step RT-PCR, according to reaction composition (Table 3).
6. Mix the solution thoroughly, and dispense aliquots of 10.4 μl into the individual PCR tubes.
7. Program Bio-Rad Real-Time PCR thermal cycler CFX96 according to the programs listed in Table 4 and Table 5.

Notably, step 4 in the above procedure includes a) incubating tubes containing nuclease-free water, forward and reverse primer pairs, and RNA template at 80° C. for 5 minutes and b) then placing the tubes on ice for 2 minutes. Table 3 also highlights an exemplary procedure for setting up the RT-qPCR reaction mix, including the high-temperature RNA denaturation step.

TABLE 3

| Aliquot 8.6 μl | Nuclease-free water | 7.4 μl |
| | Forward Primer (300 nM final contraction) | 0.6 μl |
| | Reverse Primer (300 nM final contraction) | 0.6 μl |
| 1ul (25 ng RNA) | RNA template | 1.0 μl |
| | 80° C. for 5 min, and place on ice | |
| Aliquot 10.4 μl | 2X SYBR Green RT-PCR reaction mix | 10 μl |
| | iScript reverse transcriptase for one-step RT-PCR | 0.4 μl |
| | Total | 20.0 μl |

Table 4 shows qPCR thermal cycler program for the primers of the Apsca group.

TABLE 4

| 1. 50° C. | 30 min |
| 2. 95° C. | 5 min |
| 3. 95° C. | 10 sec |
| 4. 62° C. | 30 sec |
| 5. Go to 3 for 34 cycles + plate read | |
| 6. 95° C. | 1 min |
| 7. 55° C. | 1 min |
| 8. Melt curve from 55° C. to 95° C. with 0.5° C. increments for 10 sec, plate read | |

Table 5 shows qPCR thermal cycler program for the primers of the non-Apsca group.

TABLE 5

| 1. 50° C. | 30 min |
| 2. 95° C. | 5 min |
| 3. 95° C. | 10 sec |
| 4. 61° C. | 30 sec |
| 5. Go to 3 for 34 cycles and plate read | |
| 6. 95° C. | 1 min |
| 7. 55° C. | 1 min |
| 8. Melt curve from 55° C. to 95° C. with 0.5° C. increments for 10 sec and plate read | |

Figure 4:
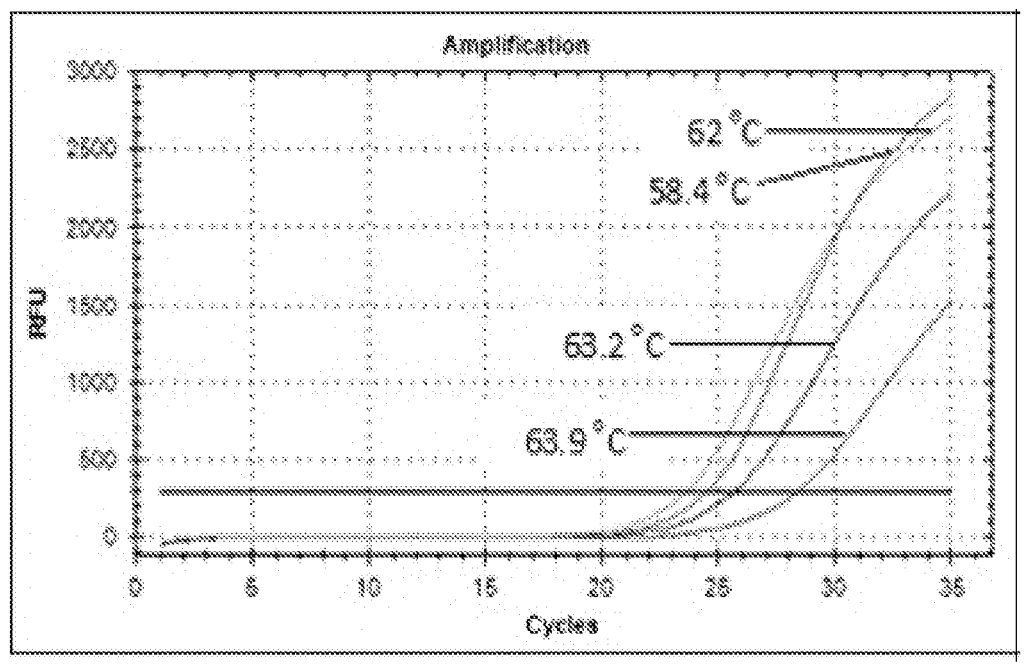
FIG. 4 shows the performance of the Apsca group primer pair on SYBR Green RT-qPCR with different annealing temperatures.
Figure 5:
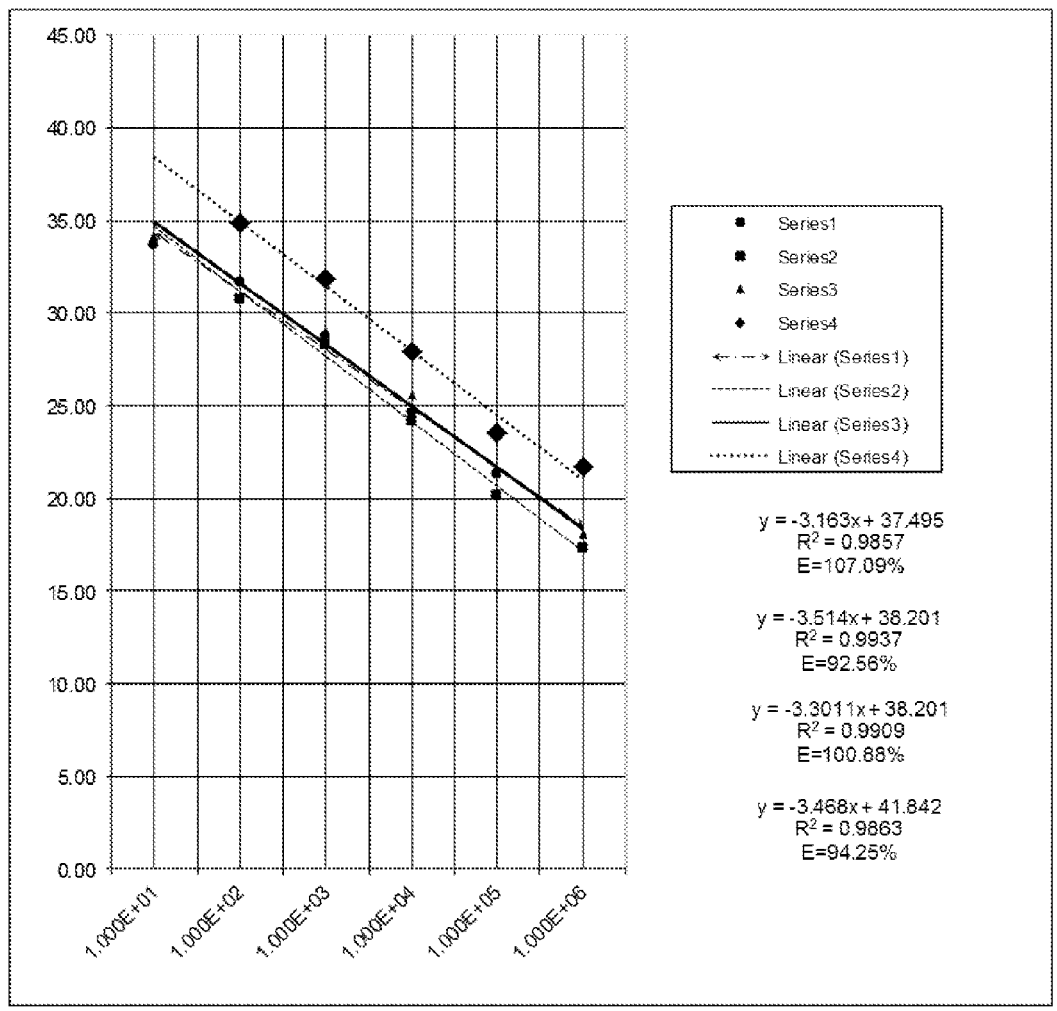
FIG. 5 shows the RT-qPCR efficiency (E) and regression analysis (regression coefficient $R^2$) of the standard curve using Apsca group primers. Series 1 represents CBLVd sample. Series 2 represents CBVd. Series 3 represents CBVd-V. Series 4 represents CBVd-VI.
Figure 6:
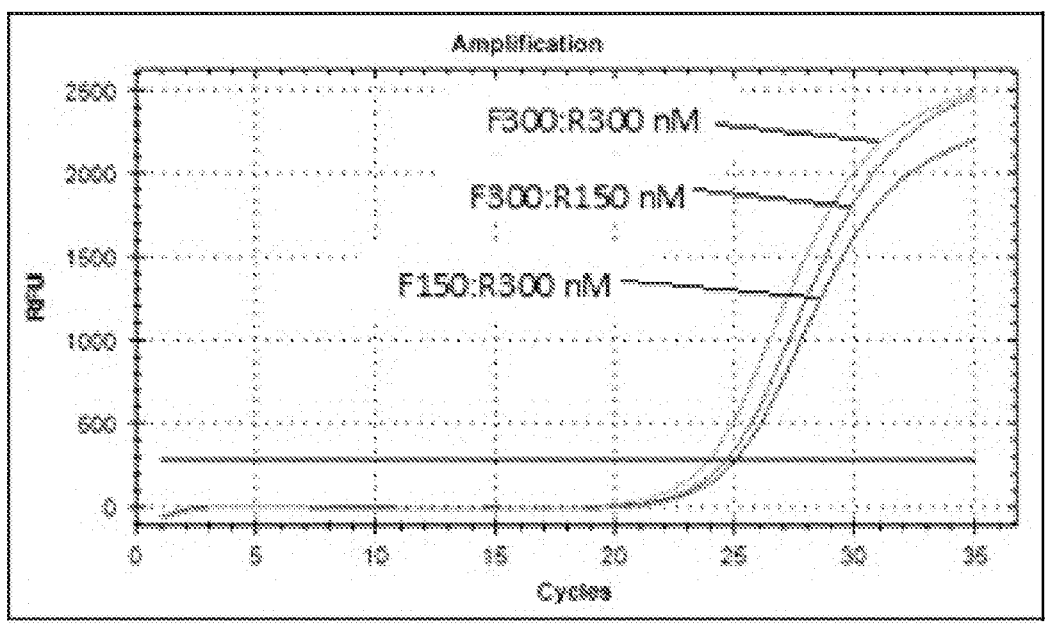
FIG. 6 shows the performance of the non-Apsca group primer pair on SYBR Green RT-qPCR with different forward and reverse primer concentrations.
Figure 7:
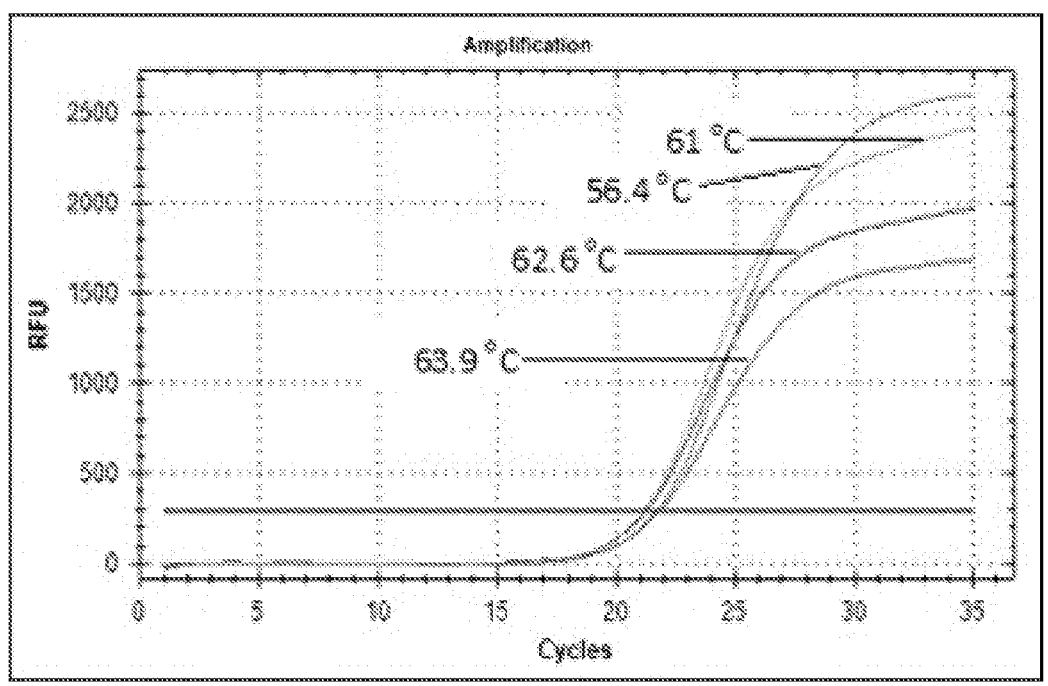
FIG. 7 shows the performance of the non-Apsca group primer pair on SYBR Green RT-qPCR with different annealing temperatures.
Figure 8:
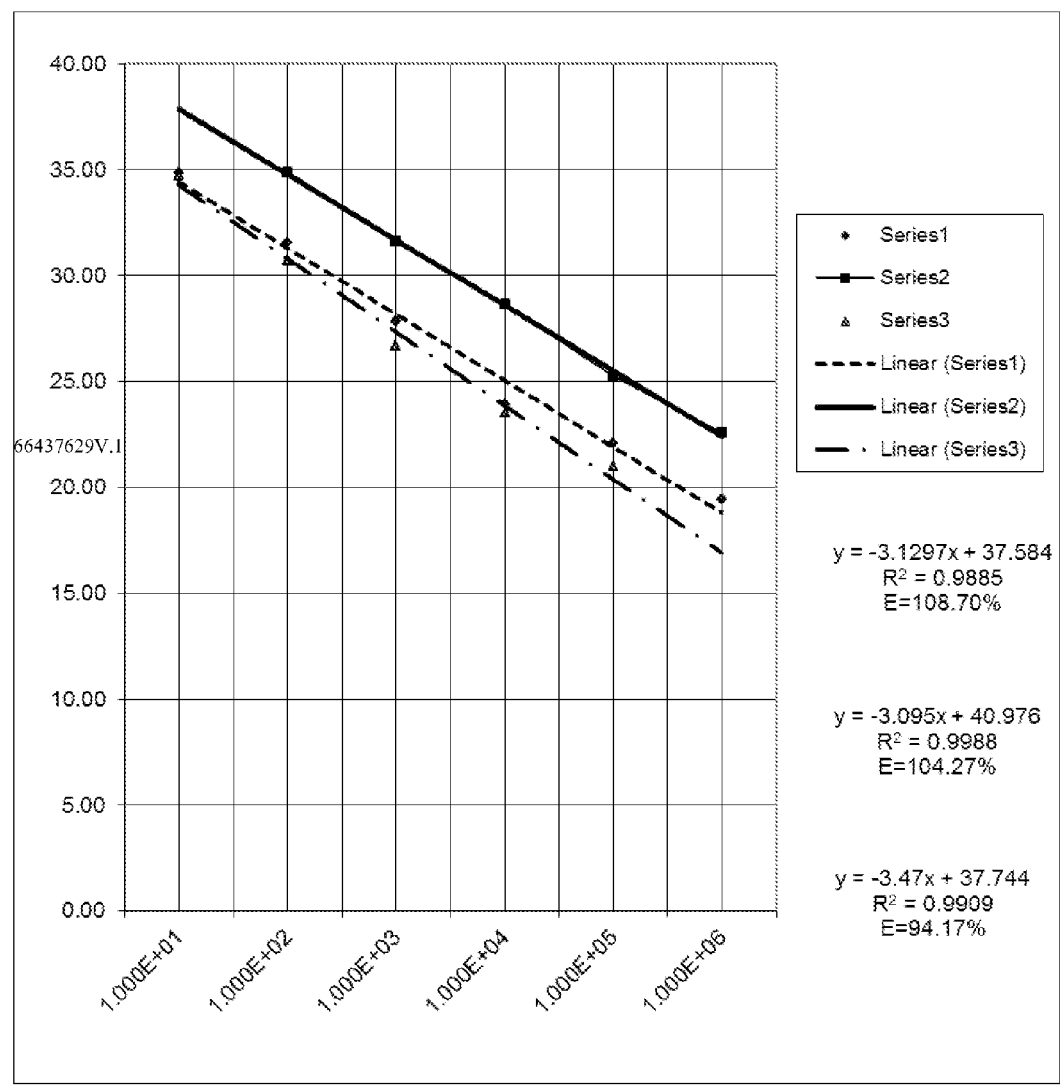
FIG. 8 shows the RT-qPCR efficiency (E) and regression analysis (regression coefficient $R^2$) of the standard curve using non-Apsca group primers. Series 1 represents HSVd sample. Series 2 represents CBCVd. Series 3 represents CEVd.

The Apsac group primers detected all the citrus viroids of the *Apscavirioid* genus. The combination of 300 nM (final concentration for each) forward and reverse primers with 62° C. of annealing and extension temperature resulted in the lowest cycles (Ct) and the highest end relative fluorescence units (RFU) values in the SYBR Green RT-qPCR assays with the primers of the Apsca group. (see, FIGS. 3 and 4). FIG. 3 shows the change in the amplification curves when the concentration of the forward and reverse primers are modified. FIG. 4 shows that the amplification curves shifts depending on the annealing temperature. To test the performance of the SYBR Green RT-qPCR assays, the RT-qPCR efficiency (E) and regression coefficient ($R^2$) were determined. Those skilled in the art recognize that the recommended or optimum values for E and $R^2$ are between 90-110% and approximately 0.98, respectively. The E and $R^2$ of the Apsca group primers in the detection of four different citrus viroid species was within the recommended limits (see, FIG. 5). The values for E and $R^2$, respectively were 107.09% and 0.9857 for CBLVd; 92.56% and 0.9937 for CDVd; 100.88% and 0.9909 for CVd-V; and 94.25% and 0.9863 for CVd-VI.

The results shows that the method described herein can be used to determine an accurate and statistically verified quantification of relative mRNA of any citrus viroids in a sample. The method of the present invention uses two set of degenerate primer pairs in separate RT-qPCR assays to detect any of the seven distinct viroid species represented in four genera of the Pospivioidae family.

All publications, patents, accession numbers, and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A diagnostic reaction mixture composition comprising a nucleic acid sample, a degenerate primer pair comprising SEQ ID NOS: 1 and 2, and/or a degenerate primer pair comprising SEQ ID NOS: 3 and 4.

2. The composition of claim 1, wherein said degenerate primer pair comprises SEQ ID NOS: 1 and 2.

3. The composition of claim 1, wherein said degenerate primer pair comprises SEQ ID NOS: 3 and 4.

4. The composition of claim 1, wherein said degenerate primer pair comprises SEQ ID NOS: 1 and 2, and wherein the mixture further comprises a second primer pair comprising SEQ ID NOS: 3 and 4.

5. The composition of claim 1, wherein said nucleic acid sample is extracted from plant material.

6. The composition of claim 1, further comprising dNTPs, a buffer, DNA polymerase, reverse transcriptase, a fluorophore, or a stabilizer.

7. A kit comprising one or more a degenerate primer pair comprising SEQ ID NOS: 1 and 2 and/or SEQ ID NOS: 3 and 4.

8. The composition of claim 5, wherein said plant material is selected from a group consisting of seed, foliage, limbs, trunk, bark, rootstock, fruit, germplasm, propagule, cuttings, and budwood.

9. The composition of claim 1, further comprising a fluorescent dye.

10. The composition of claim 1, wherein at least one primer of the degenerate primer pair is coupled to a fluorophore.

11. The kit of claim 7, wherein said degenerate primer pair comprises SEQ ID NOS: 1 and 2.

12. The kit of claim 7, wherein said degenerate primer pair comprises SEQ ID NOS: 3 and 4.

13. The kit of claim 7, wherein said degenerate primer pair comprises SEQ ID NOS: 1 and 2, and wherein the kit further comprises a second primer pair comprising SEQ ID NOS: 3 and 4.

14. The kit of claim 7, further comprising dNTPs, a buffer, DNA polymerase, reverse transcriptase, a fluorophore, or a stabilizer.

15. The kit of claim 7, further comprising a fluorescent dye.

16. The kit of claim 7, wherein at least one primer of the degenerate primer pair is coupled to a fluorophore.

* * * * *

SEQUENCE LISTING

<160> NUMBER OF SEQ ID NOS: 6

<210> SEQ ID NO 1
<211> LENGTH: 23
<212> TYPE: DNA
<213> ORGANISM: Artificial Sequence -continued

```
<220> FEATURE:
<223> OTHER INFORMATION: degenerate primer
<220> FEATURE:
<221> NAME/KEY: misc_feature
<222> LOCATION: (3)...(3)
<223> OTHER INFORMATION: "r" is a or g
<220> FEATURE:
<221> NAME/KEY: misc_feature
<222> LOCATION: (4)...(4)
<223> OTHER INFORMATION: "m" is a or c
<220> FEATURE:
<221> NAME/KEY: misc_feature
<222> LOCATION: (5)...(5)
<223> OTHER INFORMATION: "m" is a or c
<220> FEATURE:
<221> NAME/KEY: misc_feature
<222> LOCATION: (6)...(6)
<223> OTHER INFORMATION: "w" is a or t
<220> FEATURE:
<221> NAME/KEY: misc_feature
<222> LOCATION: (7)...(7)
<223> OTHER INFORMATION: "y" is c or t
<220> FEATURE:
<221> NAME/KEY: misc_feature
<222> LOCATION: (9)...(9)
<223> OTHER INFORMATION: "k" is g or t

<400> SEQUENCE: 1
garmmwyckt gtggttcctg tgg                                             23

<210> SEQ ID NO 2
<211> LENGTH: 21
<212> TYPE: DNA
<213> ORGANISM: Artificial Sequence
<220> FEATURE:
<223> OTHER INFORMATION: degenerate primer
<220> FEATURE:
<221> NAME/KEY: misc_feature
<222> LOCATION: (1)...(1)
<223> OTHER INFORMATION: "h" is a or c or t
<220> FEATURE:
<221> NAME/KEY: misc_feature
<222> LOCATION: (2)...(2)
<223> OTHER INFORMATION: "y" is c or t
<220> FEATURE:
<221> NAME/KEY: misc_feature
<222> LOCATION: (3)...(3)
<223> OTHER INFORMATION: "v" is a or c or g
<220> FEATURE:
<221> NAME/KEY: misc_feature
<222> LOCATION: (4)...(4)
<223> OTHER INFORMATION: "d" is a or g or t
<220> FEATURE:
<221> NAME/KEY: misc_feature
<222> LOCATION: (5)...(5)
<223> OTHER INFORMATION: "w" is a or t
<220> FEATURE:
<221> NAME/KEY: misc_feature
<222> LOCATION: (6)...(6)
<223> OTHER INFORMATION: "h" is a or c or t

<400> SEQUENCE: 2
hyvdwhgtcc gctcgactag c                                               21

<210> SEQ ID NO 3
<211> LENGTH: 17
<212> TYPE: DNA
<213> ORGANISM: Artificial Sequence
<220> FEATURE:
<223> OTHER INFORMATION: degenerate primer
<220> FEATURE:
<221> NAME/KEY: misc_feature
<222> LOCATION: (2)...(2)
<223> OTHER INFORMATION: "r" is a or g
<220> FEATURE:
```

```
<221> NAME/KEY: misc_feature
<222> LOCATION: (6)...(6)
<223> OTHER INFORMATION: "k" is g or t
<220> FEATURE:
<221> NAME/KEY: misc_feature
<222> LOCATION: (15)...(15)
<223> OTHER INFORMATION: "m" is a or c

<400> SEQUENCE: 3
arggakcccc ggggmaa                                                  17

<210> SEQ ID NO 4
<211> LENGTH: 22
<212> TYPE: DNA
<213> ORGANISM: Artificial Sequence
<220> FEATURE:
<223> OTHER INFORMATION: degenerate primer
<220> FEATURE:
<221> NAME/KEY: misc_feature
<222> LOCATION: (3)...(3)
<223> OTHER INFORMATION: "s" is c or g
<220> FEATURE:
<221> NAME/KEY: misc_feature
<222> LOCATION: (4)...(4)
<223> OTHER INFORMATION: "k" is g or t
<220> FEATURE:
<221> NAME/KEY: misc_feature
<222> LOCATION: (7)...(7)
<223> OTHER INFORMATION: "k" is g or t
<220> FEATURE:
<221> NAME/KEY: misc_feature
<222> LOCATION: (12)...(12)
<223> OTHER INFORMATION: "w" is a or t
<220> FEATURE:
<221> NAME/KEY: misc_feature
<222> LOCATION: (14)...(14)
<223> OTHER INFORMATION: "m" is a or c
<220> FEATURE:
<221> NAME/KEY: misc_feature
<222> LOCATION: (15)...(15)
<223> OTHER INFORMATION: "w" is a or t

<400> SEQUENCE: 4
ctskackcca gwgmwccgcg gc                                            22

<210> SEQ ID NO 5
<211> LENGTH: 318
<212> TYPE: DNA
<213> ORGANISM: Citrus bent leaf viroid

<400> SEQUENCE: 5
cggagacttc ttgtggttcc tgtggtgaca cccctcaagc cctacctgcg aaagaaaaaa    60
gtgttagaag gcggcagagg agctgactgg tcgtcgtcga cgaaggctcg tcagctgcgg   120
aggttggggt cgactggctc cggtggcgaa gttgagctct gctcttctaa gctgtaacgg   180
accggtcccc ttcacccgag cgctgcttgc cgctagtcga gcggacttcc aagtctccct   240
cccgagccgc ttttcttttc tacctaattt ccgtagcagc ggggagaggg tgaagcccct   300
gaaccnnnga gggnnncct                                                318

<210> SEQ ID NO 6
<211> LENGTH: 301
<212> TYPE: DNA
<213> ORGANISM: Hop stunt viroid

<400> SEQUENCE: 6
ctggggaatt ctcgagttgc cgcatgggca agcaaagaaa aaacaaggca gggaggagac    60
ttacctgaga aaggagcccc ggggcaactc ttctcagaat ccagcgagag gcgtaggaga   120
```

```
gagggccgcg gtgctctgga gtagaggctt ctagcttcga aacaccatcg atcgtccctt      180
cttcttttac cttctcctgg ctcttcgagt gagacgcgac cggtggcatc acctctcggt      240
tcgtcttcca acctgctttt tgtctatctg agcctctgcc cggatcctct cttgagcccc      300
t                                                                     301
```